United States Patent [19]

Jelly

[11] Plant 4,151

[45] Nov. 15, 1977

[54] ROSE PLANT SEEDLING

[75] Inventor: Robert G. Jelly, Richmond, Ind.

[73] Assignee: E. G. Hill Co., Inc., Richmond, Ind.

[21] Appl. No.: 765,396

[22] Filed: Feb. 3, 1977

[51] Int. Cl.[2] ..... A01H 5/00

[52] U.S. Cl. ..... Plt./20

[58] Field of Search ..... Plt./20, 21

*Primary Examiner*—Robert E. Bagwill

*Attorney, Agent, or Firm*—Chas. W. Rummler

[57] ABSTRACT

A red rose plant intended for greenhouse culture for the production of cut flowers, originated as a seedling of Red American Beauty (P.P. 1,982) crossed with Forever Yours (P.P. 2,443), the new plant being distinguished by its vigorous growth and free, continuous production of very large flowers having a brilliant red color which is an improvement over both parents. This new plant crops more uniformly than its seed parent and has a better flower form, it has the cropping characteristics of its pollen parent and has more shoots borne on slightly shorter stems.

1 Drawing Figure

BACKGROUND OF THE NEW PLANT

My new rose plant was developed by me at Richmond, Ind., by crossing Red American Beauty with Forever Yours in the Spring of 1966 with the object of maintaining the good cropping and productivity of the parents while improving the flower form and color of both parents. The first flower of the new plant was found by me in the Spring of 1967 and because it appeared to have the improved characteristics which I sought, the new plant was reproduced by me by grafting at Richmond, Ind. Succeeding generations of this new plant, propagated by grafting at Richmond, Ind., and by budding at Livermore, Calif., have demonstrated that its novel and distinguishing characteristics hold true from generation to generation and are firmly fixed.

DESCRIPTION OF THE DRAWING

My new variety of rose plant is illustrated by the accompanying photographic drawing which, in full color, shows a fully opened flower and three stages of the buds, typical leaves, a specimen of young wood with leaves and a piece of old stem, the colors shown being as nearly true as can be reasonably obtained by conventional photographic procedures.

DESCRIPTION OF THE NEW PLANT

The following is a detailed description of the new plant from observations of greenhouse plants made at Richmond, Ind., the color descriptions being according to the Horticultural Colour Chart (HCC), produced by Robert S. Wilson in collaboration with the British Colour Council, or the Royal Horticultural Society Colour Chart (RHS), published by The Royal Horticultural Society of London, England.

THE PLANT

Origin: Seedling.

Parentage: Seed parent — Red American Beauty (P.P. 1,982). Pollen parent — Forever Yours (P.P. 2,443).

Class: Hybrid Tea.

Type: Greenhouse grandiflora for cut flowers.

Habit: Upright and much branched.

Growth: Moderately free and vigorous.

*Canes.*—Medium in diameter.

*Main Stems.*—Color: Slightly brighter than a shade between Spinach Green 0960 and 0960/1 (HCC).

*Thorns.*—Few to several, some short and some long, downwardly hooked from a long narrow base. Color: Greyed Orange 165B, penciled with 165A (RHS).

*Prickles.*—Few, very short and stubby. Color: Greyed Orange 165B (RHS).

*Hairs.*—None.

Branches:

*Color.*—Yellow Green 144B (RHS).

*Thorns.*—Few, some branches with none, short to medium in length, hooked downward from a long narrow base. Color: Greyed Red 181D (RHS) at base to translucent at the tip.

*Prickles.*—Few on branches with no thorns and many on branches having thorns. Color: Greyed Red 182D (RHS) at the base to translucent at the tip.

*Hairs.*—None.

Foliage: Quantity — Average.

*Leaves.*—Compound of 3 to 7 leaflets, normally large in size.

*Leaflets.*—Shape: Elliptical, with cuspidate apex, acute base, and serrate margin. Aspect: Thick and leathery. Color: Young leaves: Upper surface — Fern Green 0862/3 (HCC) along the midvein but tinted immediately with a blend of Purple Madder 1028/1 and 1028 and a line of 1028 (HCC) on the margin. Under surface — A shade between Greyed Purple 183C and 183D (RHS) with a margin of Purple Madder 1028 (HCC). Mature leaves: Upper surface — A shade slightly lighter than Green 135A (RHS) but darker than Spinach Green 0960 (HCC). Under surface — A shade slightly darker and brighter than Sage Green 00861/1 but not as dark as 00861 (HCC).

*Rachis.*—Size — Medium. Upper side: Grooved and prickly. Under side: Prickly with a few thorns on some rachis.

*Stipules.*—Moderately short and narrow, some with points which are short to medium in length. Stipules turn out at an angle of about 45° and some are recurved toward the stem.

THE BUD

Before the calyx breaks:

*Size.*—Medium large to large.

*Form.*—Short pointed to globular with conspicuous neck, with foliaceous appendages on the surface of the bud, and with slender bristle-like foliaceous parts extending beyond the tip of the bud for a distance of about three-quarters or more of its length.

*Color of calyx.*—The entire body of the calyx is mottled with shades of Yellow Green 144A and 144B (RHS) and a shade slightly darker than Scheeles Green 860 (HCC) but lighter than Spinach Green 0960 (HCC) to foliaceous parts of Lettuce Green 861/3 (HCC) with pencil line of Red 47B (RHS) at the margin.

As calyx breaks:

*Outside petal color.*—Chrysanthemum Crimson 824 to Maroon 1030 (HCC).

As first petal opens:

*Bud size.*—Medium large. Form: Long pointed.

*Color of outside petal.*—A shade slightly darker than Red 53A (RHS). Inside has a shade darker and brighter than Cardinal Red 822 (HCC).

Opening character: The bud opens up well in greenhouse with a balled center.

Sepals: Permanent and of moderately long length.

*Color.*—Inside — Shades of both Yellow Green 147B and 147C (RHS) highlighted with Pea Green 61/3 (HCC) at the base and along midvein. Outside — Blotches of shades of Yellow Green 144A and 144B (RHS) with highlights of Yellow Green 144C (RHS) at the base.

Peduncle: Size — Long in length and medium to large in diameter.

*Strength.*—Erect, some being strong and some medium strong.

*Bark.*—Smooth. Color: A shade slightly lighter than Yellow Green 144A (RHS) but darker than Lettuce Green 861 (HCC).

*Prickles.*—Few on peduncle. Color: Translucent at the base to a tip of Greyed Purple 185B (RHS).

*Thorns and hairs.*—None on peduncle.

THE FLOWER

Blooming habit: Continuous and free blooming in greenhouse.

Size of bloom: Very large — 4½ to 5 inches when fully opened.

Borne: One to a stem in regular clusters on long, moderately strong to medium strong stems that tend to be weak during low light periods.

Shape: High centered at first, becoming flat as bloom matures. The petals remain loosely cupped inward at first and become rolled outward at maturity.

Petalage: Very double with 35 to 40 petals regularly arranged.

Shape of petals:

*Outside petals.*—Oval-shaped with apex of some mucronate with 1 or 2, or no notches.

*Intermediate petals.*—Oval with mucronate apex, some with one notch or none.

*Inside petals.*—Obovate with mucronate apex, some with one notch.

Texture: Moderately thick.

Aspect: Velvety inside and satiny outside.

Color:

The following description relates to a rose newly opened in a greenhouse in March, 1975.

*Outside petals.*—Outer surface: A shade between Cardinal Red 0822/3 and 0822/2 (HCC). Inside surface: A velvety and brilliant tone of a shade between Currant Red 821 and Cardinal Red 822/1 (HCC).

*Intermediate petals.*—Outer surface: Slightly darker than Red 53B (RHS). Inside surface: A shade slightly darker than Cardinal Red 822/1 (HCC) but not as dark as Red 53A (RHS) and more brilliant than either color.

*Inner Petals.*—Outer surface: A shade slightly darker than Rose Red 724 (HCC). Inside surface: A shade between Currant Red 821/1 and Cardinal Red 822/1 (HCC) but more brilliant and velvety than either color.

This description relates to a flower opened for 3 days in greenhouse in March, 1975.

*Outside petals.*—Outer surface: Slightly darker than Chrysanthemum Crimson 824/3 but brighter than Currant Red 821 (HCC). Inside surface: A blend between Rose Red 724 and Currant Red 821 (HCC).

*Intermediate petals.*—Outer surface: More brilliant than Cardinal Red 822/3 (HCC). Inside surface: A shade between Rose Red 724 and Cardinal Red 822/3 (HCC) but more velvety than either color.

*Inner petals.*—Outer surface: A shade slightly darker and more brilliant than Cardinal Red 822/2 (HCC). Inside surface: A shade slightly darker and more velvety than Cardinal Red 822/3 with highlights of Rose Red 724 (HCC).

General color effect:

*Newly opened flower.*—A shade of Currant Red 821 and 821/1 but more brilliant and more velvety than either color.

*Three days opened flower.*—Shades of Currant Red 821/1 with highlights of Rose Red 724 (HCC).

Note: The flower colors stated may be modified by being shaded with other colors.

Effect of weather: In hot weather the petal colors fade to a shade slightly lighter than Currant Red 821/1 (HCC); and in cold weather the colors fade to a shade slightly darker than Currant Red 821 (HCC).

Persistence: Petals hang on and dry.

Fragrance: Strong, spicey.

Lasting quality: Seven days at living room temperature in February 1975.

REPRODUCTIVE ORGANS

Stamens: Many in number arranged irregularly about the pistils and mixed with petaloids.

*Filaments.*—Some are short and some are long and most have anthers. Color: A shade between Currant Red 821/3 and 821/2 (HCC).

*Anthers.*—Very large and all open at once. Color: The pollen cup is a shade between Greyed Orange 175A and 175B (RHS) and is bordered by a shade slightly lighter than Greyed Orange 163A (RHS).

*Pollen.*—Moderate in amount. Color: Yellow Orange 21B (RHS).

Pistils: Medium in number.

*Styles.*—Uneven, very thin; of medium length and bunched. Color: A shade between Green Yellow 1D and 2D (RHS) at the base to a shade of Red 53B and 53C (RHS) directly under the stigma.

*Stigmas.*—Color — Shades of Yellow Orange 18A and Yellow Orange 20B (RHS).

Ovaries: Some protruding from the calyx.

Hips: Medium long with a conspicuous neck, pear shaped and moderately rough with thick and fleshy walls.

*Color.*—Spanish Orange 010 (HCC) at top and bottom, the center being patched with both Greyed Orange 164B and Greyed Orange 166B (RHS).

Seeds: Average in number and of medium size.

This new variety of rose plant has picked up the cropping characteristics of its pollen parent, Forever Yours, and has more shoots borne on slightly shorter stems, it crops more uniformly than its seed parent, Red American Beauty, and has a better flower form. The new variety is a vigorous grower and has a brilliant red color which is an improvement over both of its parents.

I claim:

1. A new and distinct red rose cultivar substantially as herein shown and described, characterized by the brilliant red color of its very large blossoms, its vigorous habit of growth, its retention of the good cropping characteristics of its pollen parent, and its improved flower form over that of its seed parent.

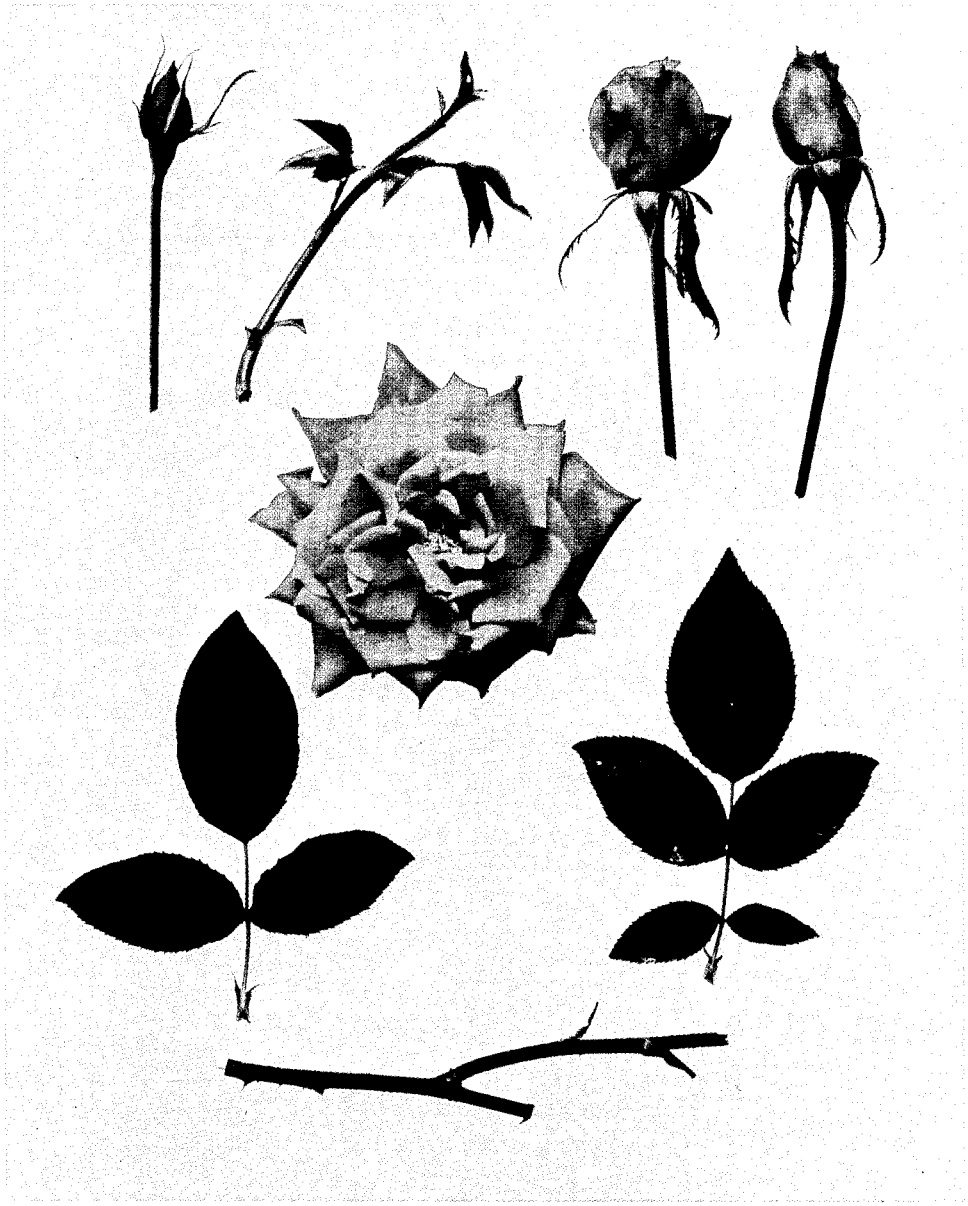

* * * * *